(12) United States Patent
Hopkins

(10) Patent No.: US 7,047,572 B2
(45) Date of Patent: May 23, 2006

(54) DISPOSABLE PANT HAVING AN INWARD CROTCH SEAM AND METHOD OF MAKING SAME

(75) Inventor: Heidi Bauerlein Hopkins, Neenah, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 432 days.

(21) Appl. No.: 10/036,664

(22) Filed: Dec. 21, 2001

(65) Prior Publication Data

US 2003/0115660 A1 Jun. 26, 2003

(51) Int. Cl.
*A41D 9/00* (2006.01)

(52) U.S. Cl. ............................. 2/400; 2/403; 604/385.01
(58) Field of Classification Search ...................... 2/400, 2/402, 403, 404, 406, 407, 243.1; 604/385–400
See application file for complete search history.

(56) References Cited

U.S. PATENT DOCUMENTS

| | | | | |
|---|---|---|---|---|
| 3,560,292 | A | * | 2/1971 | Butter ........................ 156/229 |
| 3,739,398 | A | * | 6/1973 | Sarmiento ...................... 2/407 |
| 4,100,324 | A | | 7/1978 | Anderson et al. |
| 4,145,763 | A | | 3/1979 | Abrams et al. |
| 4,302,853 | A | * | 12/1981 | Mesek ........................... 2/402 |
| 4,427,408 | A | | 1/1984 | Karami et al. |
| 4,610,681 | A | * | 9/1986 | Strohbeen et al. .......... 604/396 |
| 4,646,362 | A | | 3/1987 | Heran et al. |
| 4,663,220 | A | | 5/1987 | Wisneski et al. |
| 4,940,464 | A | | 7/1990 | Van Gompel et al. |
| 5,046,272 | A | | 9/1991 | Vogt et al. |
| 5,104,116 | A | | 4/1992 | Pohjola |
| 5,224,405 | A | | 7/1993 | Pohjola |
| 5,226,992 | A | | 7/1993 | Morman |
| 5,546,608 | A | | 8/1996 | Russano |
| 5,746,730 | A | | 5/1998 | Suzuki et al. |

FOREIGN PATENT DOCUMENTS

| EP | 0 217 032 B1 | 2/1992 |
|---|---|---|
| EP | 0 417 766 B1 | 4/1994 |

* cited by examiner

*Primary Examiner*—Gloria M. Hale
(74) *Attorney, Agent, or Firm*—Thomas M. Gage; H. Michael Kubicki; Denise L. Stoker

(57) ABSTRACT

A method of making a disposable pant having an inward fin crotch seam includes providing first and second panels, each panel having an inner surface, an outer surface, a panel waist edge, a panel leg edge, and two side regions. The panels are positioned such that their respective outer surfaces are in a facing relationship. The panels are bonded together to form a crotch seam. The panels are repositioning such that the inner surfaces are in a facing relationship. The side regions of the first panel are bonded to the side regions of the second panel to create two side seams to define a waist opening and two leg openings. The crotch seam may be inset toward the panel waist edges, and may include one or more slits. The disposable pant may include an absorbent.

31 Claims, 11 Drawing Sheets

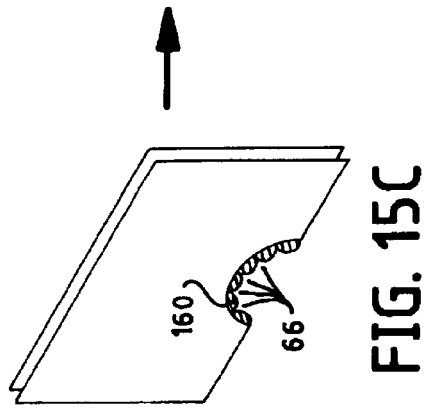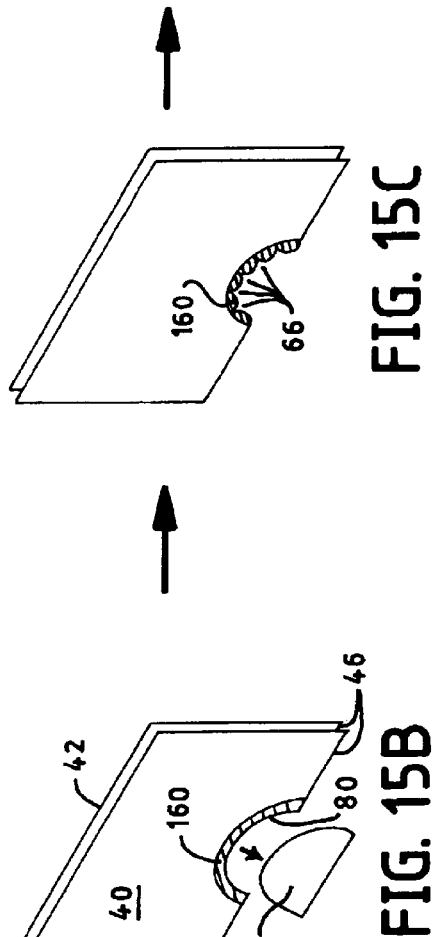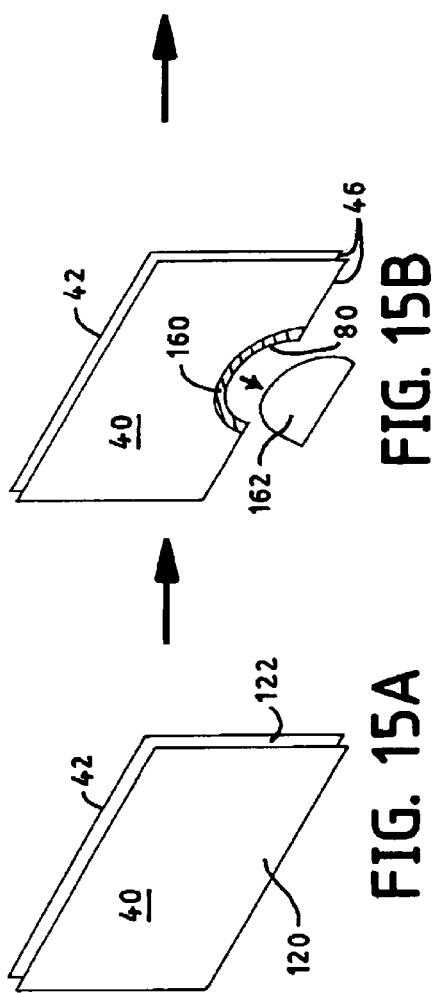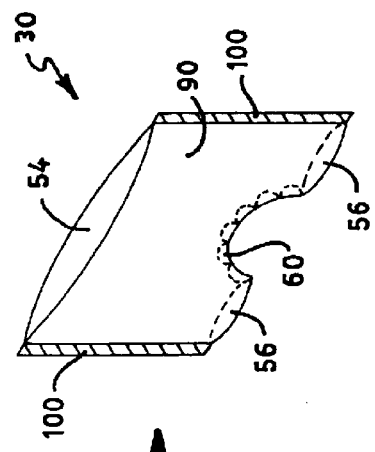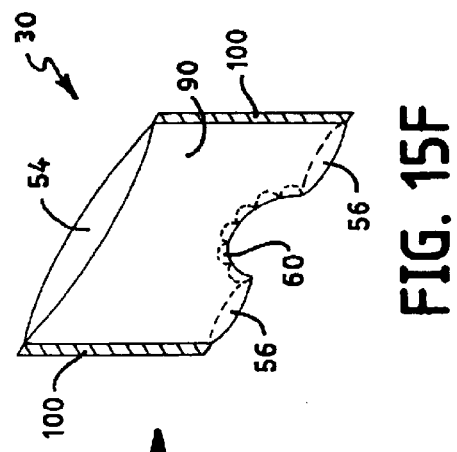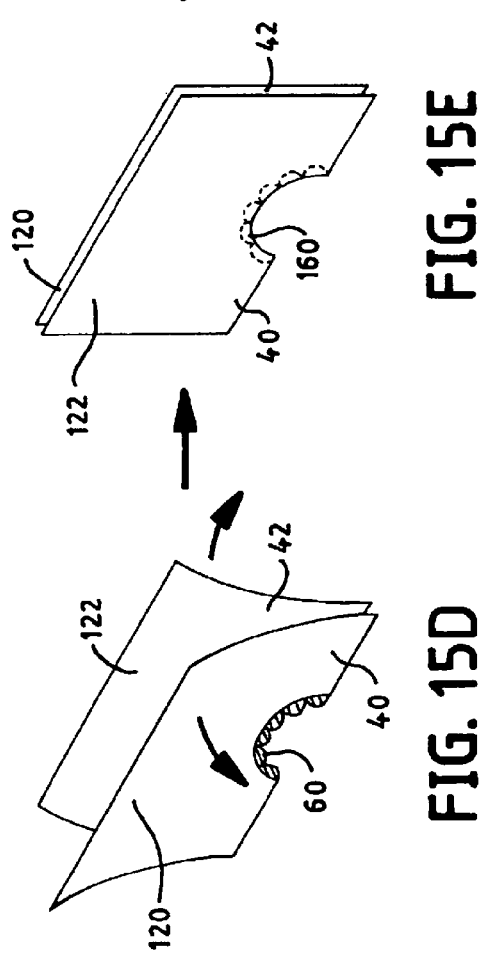

DISPOSABLE PANT HAVING AN INWARD CROTCH SEAM AND METHOD OF MAKING SAME

BACKGROUND OF THE INVENTION

The present invention pertains to disposable pants having inward crotch seams and methods of making such pants.

Pant-like disposable garments have numerous applications including disposable clothing, training pants, feminine care products, adult incontinence products, disposable swimwear, or the like. Pant-like disposable garments are typically three-dimensional products with closed sides so that the product has a unitary waist opening and two leg openings. The wearer raises and lowers the garment to apply the product. Three-dimensional, pant-like products are particularly appealing because the pant has a very garment-like look.

Many disposable pants are formed as composite structures in which several components are combined to form a product specifically suited to its intended purpose. For example, disposable pants often include one or more absorbent materials intended to absorb various bodily exudates such as urine, menstrual fluid, and sweat. Such products may include a liquid permeable bodyside liner and a liquid impermeable outer cover, and can include other materials and features such as elastic materials and containment structures.

However, many disposable pants are aesthetically unappealing. Existing disposable absorbent pants are often overly bulky and often resemble disposable baby diapers. Various attempts have been made to provide disposable pants having an improved, more clothing-like appearance. However, disposable pants, particularly disposable absorbent pants, present many manufacturing challenges. In part, this is due to the high speed that is necessary to economically produce relatively low-cost disposable absorbent products. Often, product design is compromised by cost and manufacturing constraints, with the result that disposable pants often lack aesthetic appeal and product function.

Thus, what is lacking and needed in the art are garment-like, aesthetically appealing disposable pants, as well as methods of efficiently manufacturing such pants.

SUMMARY OF THE INVENTION

In response to the above-referenced unfulfilled need in the art, new disposable pants, and methods for manufacturing such pants, have been invented. One aspect of the invention pertains to a method of making a disposable pant having an inward fin crotch seam. One embodiment of the method comprises providing first and second panels, each panel having an inner surface, an outer surface, a panel waist edge, a panel leg edge, and two side regions; positioning the panels such that their respective outer surfaces are in a facing relationship; bonding the panels together to form a crotch seam; repositioning the panels such that the inner surfaces are in a facing relationship; and bonding the side regions of the first panel to the side regions of the second panel to create two side seams to define a waist opening and two leg openings.

Another embodiment of the method of making a disposable pant having an inward fin crotch seam comprises providing first and second panels, each panel having an inner surface, an outer surface, a panel waist edge, a panel leg edge, and two side regions; positioning the panels such that their respective outer surfaces are in a facing relationship; bonding the panels together remote from the panel leg edges to form an inset crotch seam; removing sections of the panels between the inset crotch seam and the panel leg edges to define an outer crotch edge; repositioning the panels such that the inner surfaces are in a facing relationship; and bonding the side regions of the first panel to the side regions of the second panel to create two side seams to define a waist opening and two leg openings.

Yet another embodiment of the method of method making a disposable pant having an inward fin crotch seam comprises providing first and second panels, each panel having an inner surface, an outer surface, a panel waist edge, a panel leg edge, and two side regions; positioning the panels such that their respective outer surfaces are in a facing relationship; bonding the panels together to form a crotch seam having a crotch seam edge; cutting at least one slit in the crotch seam to define at least two crotch seam sections, each section having a crotch seam section edge; repositioning the panels such that the inner surfaces are in a facing relationship; and bonding the side regions of the first panel to the side regions of the second panel to create two side seams to define a waist opening and two leg openings.

Still another embodiment of making disposable pants having inward fin crotch seams comprises providing first and second webs, each web having a longitudinal direction, a transverse direction, an inner surface, an outer surface, a web waist edge generally aligned with the longitudinal direction, and a web leg edge generally aligned with the longitudinal direction; positioning the webs such that their respective outer surfaces are in a facing relationship; bonding the webs together at a plurality of locations in the longitudinal direction to define a plurality of crotch seams, creating an inside-out composite pant web; repositioning the webs such that the inner surfaces are in a facing relationship, creating an outside-out composite pant web having a plurality of inward fin crotch seams spaced apart in the longitudinal direction; bonding the webs together at a plurality of locations in the longitudinal direction to define a plurality of web side seams, each web side seam positioned longitudinally between a pair of crotch seams; and cutting the outside-out composite pant web into a plurality of disposable pants, each pant having a waist opening, two leg openings, two pant side seams, and an inward fin crotch seam.

Another aspect of the present invention pertains to a disposable pant having a waist opening, two leg openings, and two side regions. One embodiment of the pant comprises front and back panels, two side seams joining the front and back panels, and an inward fin crotch seam joining the front and back panels. In particular embodiments, the disposable pant includes an absorbent.

The present invention relates to a wide variety of absorbent and non-absorbent pants, including training pants, swim pants, diaper pants, incontinence garments, feminine care products, health care garments, apparel for institutional, industrial and consumer use, or other garments. Disposable absorbent pants are adapted to be worn adjacent to the body of a wearer to absorb and contain various exudates discharged from the body.

DEFINITIONS

Within the context of this specification, each term or phrase below will include the following meaning or meanings.

"Bonded" refers to the joining, adhering, connecting, attaching, or the like, of two elements. Two elements will be considered to be bonded together when they are bonded directly to one another or indirectly to one another, such as when each is directly bonded to intermediate elements.

"Comprising" is inclusive or open-ended and does not exclude additional, unrecited elements or method steps.

"Connected" refers to the joining, adhering, bonding, attaching, or the like, of two elements. Two elements will be considered to be connected together when they are connected directly to one another or indirectly to one another, such as when each is directly connected to intermediate elements.

"Disposable" refers to articles which are designed to be discarded after a limited use rather than being laundered or otherwise restored for reuse.

"Elastic," "elasticized" and "elasticity" mean that property of a material or composite by virtue of which it tends to recover its original size and shape after removal of a force causing a deformation.

"Elastomeric" refers to a material or composite which can be elongated by at least 25 percent of its relaxed length and which will recover, upon release of the applied force, at least 10 percent of its elongation. It is generally preferred that the elastomeric material or composite be capable of being elongated by at least 100 percent, more preferably by at least 300 percent, of its relaxed length and recover, upon release of an applied force, at least 50 percent of its elongation.

"Fabrics" is used to refer to all of the woven, knitted and nonwoven fibrous webs.

"Flexible" refers to materials which are compliant and which will readily conform to the general shape and contours of the wearer's body.

"Hydrophilic" describes fibers or the surfaces of fibers which are wetted by the aqueous liquids in contact with the fibers. The degree of wetting of the materials can, in turn, be described in terms of the contact angles and the surface tensions of the liquids and materials involved. Equipment and techniques suitable for measuring the wettability of particular fiber materials or blends of fiber materials can be provided by a Cahn SFA-222 Surface Force Analyzer System, or a substantially equivalent system. When measured with this system, fibers having contact angles less than 90° are designated "wettable" or hydrophilic, while fibers having contact angles greater than 90° are designated "nonwettable" or hydrophobic.

"Integral" is used to refer to various portions of a single unitary element rather than separate structures bonded to or placed with or placed near one another.

"Layer" when used in the singular can have the dual meaning of a single element or a plurality of elements.

"Liquid impermeable", when used in describing a layer or multi-layer laminate, means that a liquid, such as urine, will not pass through the layer or laminate, under ordinary use conditions, in a direction generally perpendicular to the plane of the layer or laminate at the point of liquid contact. Liquid, or urine, may spread or be transported parallel to the plane of the liquid impermeable layer or laminate, but this is not considered to be within the meaning of "liquid impermeable" when used herein.

"Member" when used in the singular can have the dual meaning of a single element or a plurality of elements.

"Nonwoven" and "nonwoven web" refer to materials and webs of material which are formed without the aid of a textile weaving or knitting process.

"Operatively joined," with reference to the attachment of an elastic member to another element, means that the elastic member when attached to or connected to the element, or treated with heat or chemicals, by stretching, or the like, gives the element elastic properties; and with reference to the attachment of a non-elastic member to another element, means that the member and element can be attached in any suitable manner that permits or allows them to perform the intended or described function of the joinder. The joining, attaching, connecting or the like can be either directly, such as joining either member directly to an element, or can be indirectly by means of another member disposed between the first member and the first element.

"Permanently bonded" refers to the joining, adhering, connecting, attaching, or the like, of two elements of an absorbent garment such that the elements tend to be and remain bonded during normal use conditions of the absorbent garment.

"Stretch bonded" refers to an elastic member being bonded to another member while the elastic member is extended at least about 25 percent of its relaxed length. Desirably, the term "stretch bonded" refers to the situation wherein the elastic member is extended at least about 100 percent, and more desirably at least about 300 percent, of its relaxed length when it is bonded to the other member.

"Stretch bonded laminate" refers to a composite material having at least two layers in which one layer is a gatherable layer and the other layer is an elastic layer. The layers are joined together when the elastic layer is in an extended condition so that upon relaxing the layers, the gatherable layer is gathered.

"Surface" includes any layer, film, woven, nonwoven, laminate, composite, or the like, whether pervious or impervious to air, gas, and/or liquids.

These terms may be defined with additional language in the remaining portions of the specification.

BRIEF DESCRIPTION OF THE DRAWINGS

The above-mentioned and other features of the present invention and the manner of attaining them will become more apparent, and the invention itself will be better understood by reference to the following description and the accompanying drawings, wherein similar features in different figures have been given the same reference numeral.

FIGS. 15a–f are perspective views of various stages of one embodiment of the method according to the present invention.

DETAILED DESCRIPTION OF THE PREFERRED EMBODIMENTS

Figure 1:
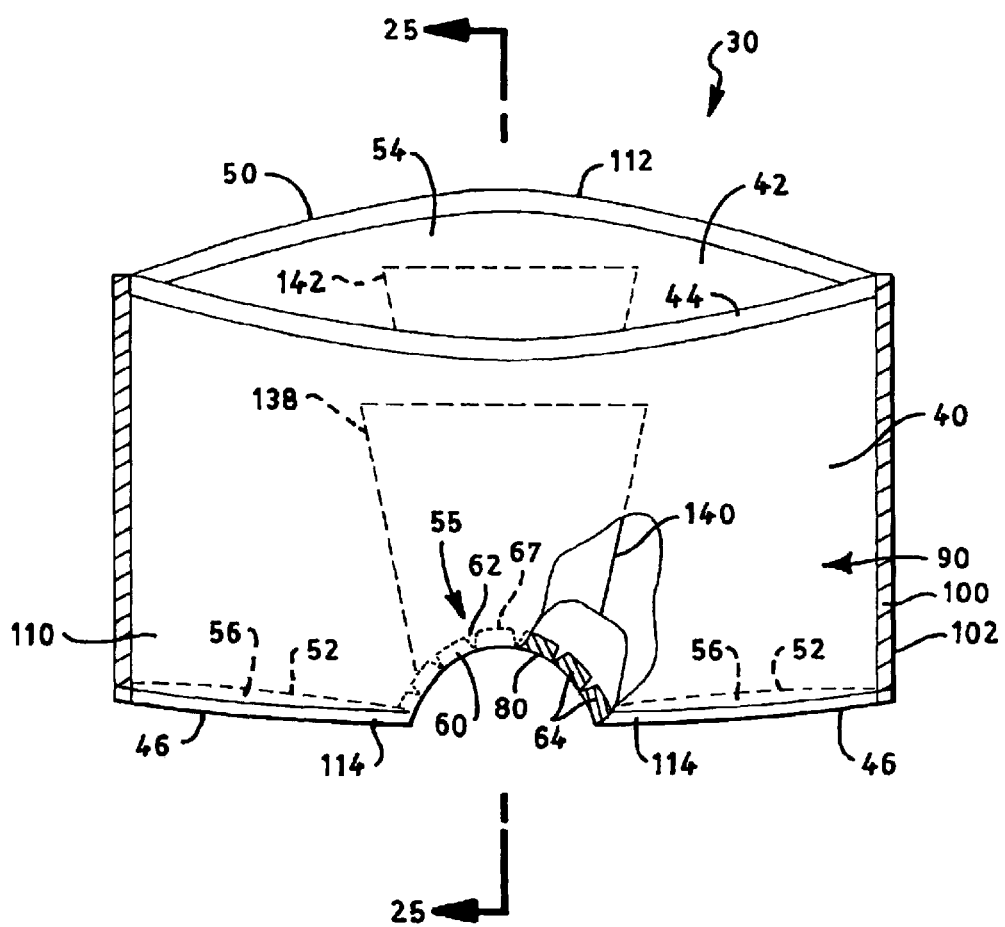
FIG. 1 is a perspective view of an exemplary embodiment of the disposable pant according to the present invention, with portions cut away to show the underlying features.
Figure 2:
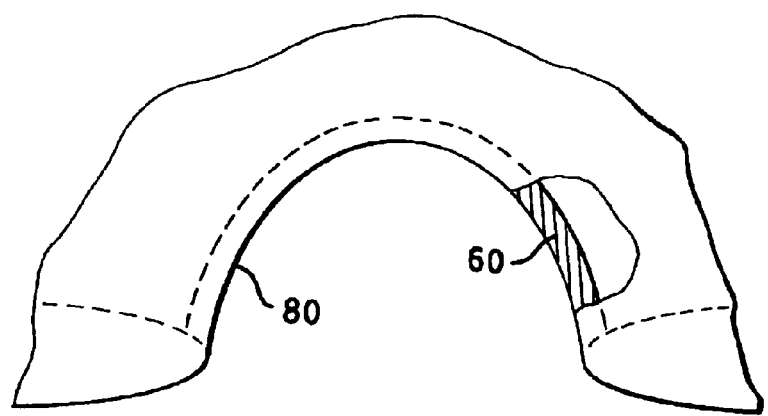
FIG. 2 is an enlarged view of a region of an alternative embodiment of the disposable pant of FIG. 1, with portions cut away to show the underlying features.

As representatively illustrated in FIG. 1, an embodiment of a disposable pant 30 of the present invention can include a first panel 40, a second panel 42, a crotch region 55, an inward fin crotch seam 60, an outer crotch edge 80, panel side regions 90, side seams 100, side edges 102, and leg sleeves 110. The first panel 40 defines a first panel waist edge 44 and a two first panel leg edges 46. The second panel 42 defines a second panel waist edge 50 and two second panel leg edges 52. The pant 30 has a waist opening 54 and two leg openings 56. The disposable pant 30 can, but need not, include a waist cuff 112 and leg cuffs 114. In particular embodiments, the disposable pant 30 can include an absorbent structure 138, such as, for example, absorbent panels 140 and 142. Various embodiments of these and other features will now be described.

Figure 14:
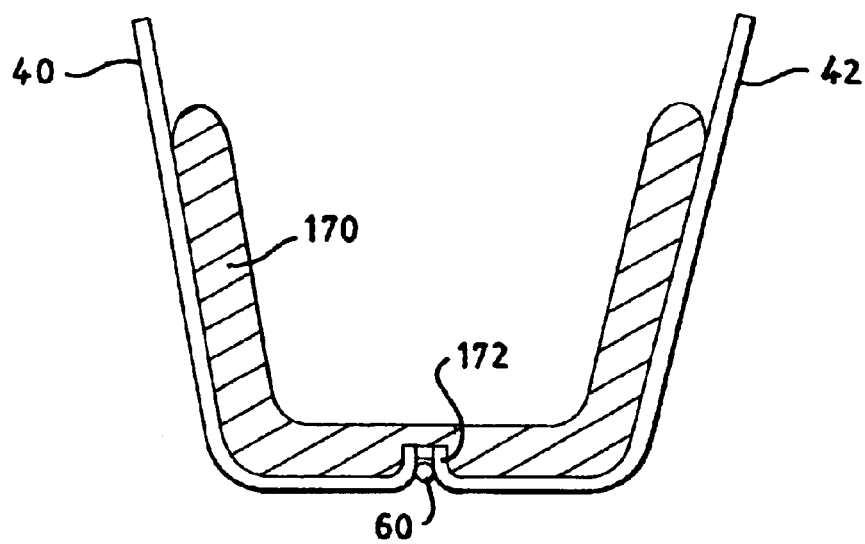
FIG. 14 is a section view of an alternative embodiment of the pant of FIG. 1 taken from the plane of line 25—25 in FIG. 1.

The disposable pant 30 includes an outer crotch edge 80. In particular embodiments, the outer crotch edge 80 follows a path at least a part of which is inset, as illustrated in FIGS. 1–4. "Inset," as used herein to describe a crotch seam or edge, means that at least part of the seam or edge is recessed toward the waist edges 44 and 50 of the panels 40 and 42 relative to the leg edges 46 and 52 of the panels 40 and 42. For example, the outer crotch edge 80 can follow a path which begins at one leg opening 56, extends toward the waist opening 54, and terminates at the other leg opening 56. In particular embodiments, as representatively illustrated in FIGS. 14, the path is arcuate. In other embodiments, the path of the outer crotch edge 80 can be straight, arcuate, or any combination of one or more straight and/or arcuate segments. It should be noted that the outer crotch edge 80 can follow a path which follows a generally straight line between leg edges 46 and 52 of opposite leg openings 56, as illustrated in FIG. 5. In such an embodiment, the outer crotch edge 80 may or may not be inset toward the waist edges 44 and 50 relative to the leg edges 46 and 52. In yet another embodiment, representatively illustrated in FIG. 8, the outer crotch edge 80 follows a path which begin at one leg opening 56, extends away from the waist opening 54, and terminates at the other leg opening 56.

Figure 11:
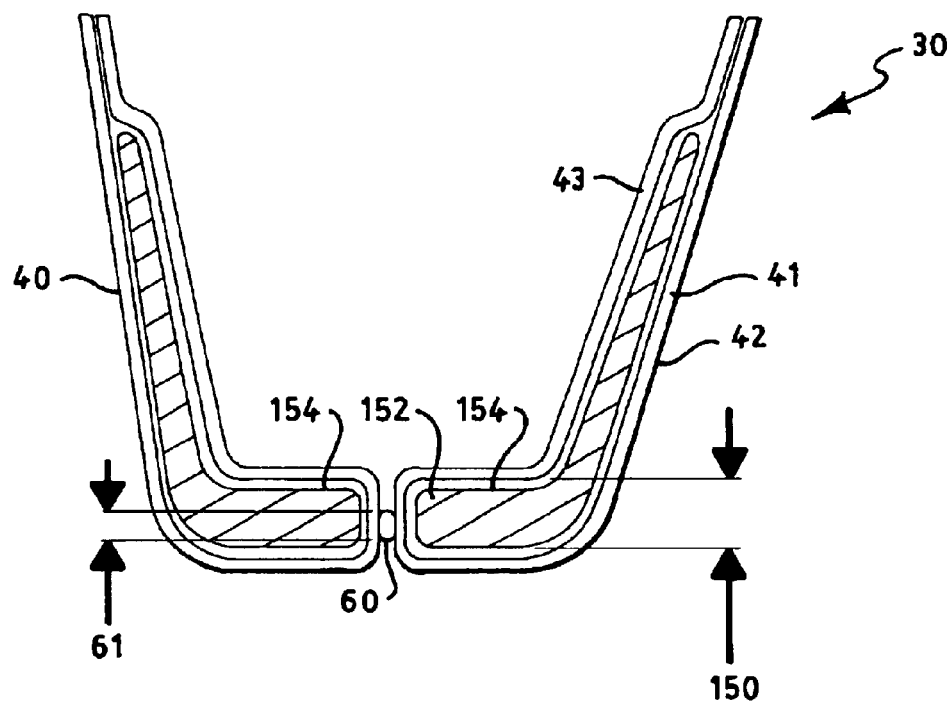
FIG. 11 is a section view of one embodiment of the pant of FIG. 1 taken from the plane of line 25—25 in FIG. 1.

The disposable pant 30 also includes an inward fin crotch seam 60 which connects the first panel 40 and the second panel 42. The cross-hatching within the inward fin crotch seam 60 in the Figures denotes the region in which the first panel 40 and second panel 42 are bonded to one another. The inward fin crotch seam 60 can take a variety of forms, as representatively illustrated in FIGS. 1–9. As used herein, "inward," when used to describe a fin seam, means that the terminal edges of the bonded materials are disposed toward the interior of the fully assembled pant. For example, as representatively illustrated in FIGS. 1, 8 and 11, an inward fin crotch seam 60 has its terminal edges disposed toward the interior of the pant 30, and in these particular configurations has the bonded area sandwiched between panels 40 and 42. Desirably, the crotch seam 60, and in particular embodiments the terminal edges, are hidden from view while the product is donned by virtue of its inward position. In certain embodiment, the inward terminal edges of the panels 40 and 42 together define a crotch seam edge 67. As shall be seen, the panels 40 and 42 may or may not be connected along the crotch seam edge.

Figure 8:
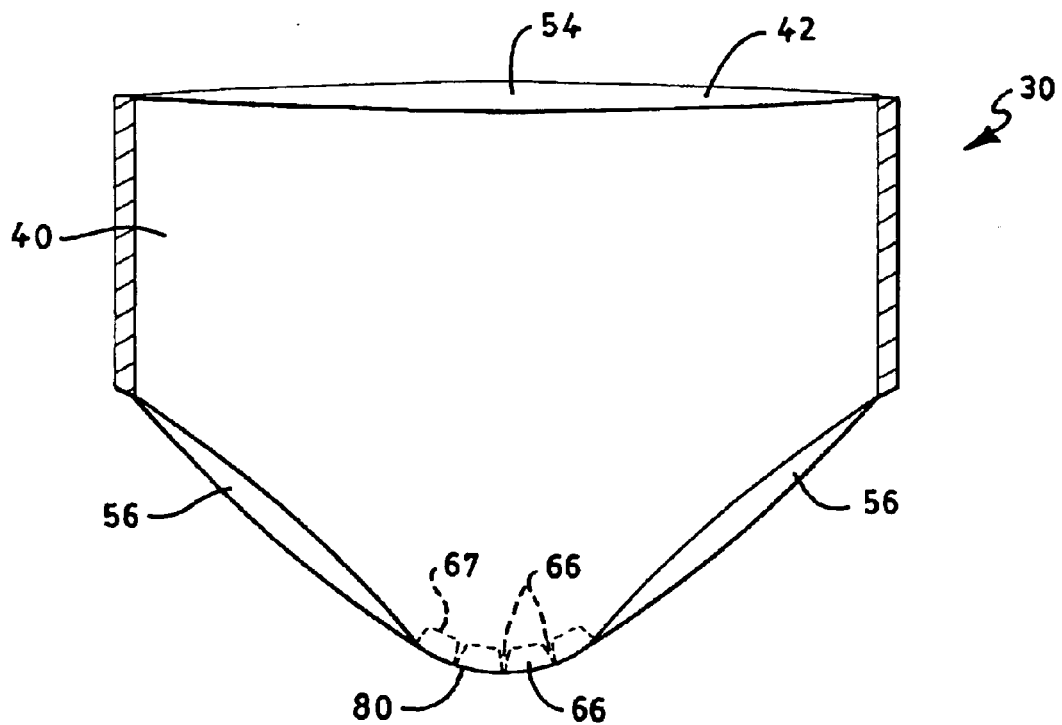
FIG. 8 is a perspective view of an alternative embodiment of the disposable pant according to the present invention.
Figure 9:
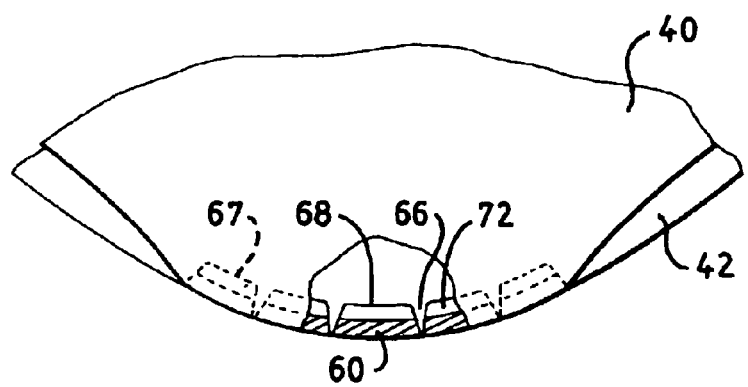
FIG. 9 is an enlarged view of a region of an alternative embodiment of the disposable pant of FIG. 8, with portions cut away to show the underlying features.

As illustrated in FIGS. 1–4, the inward fin crotch seam 60 can follow an arcuate path. For example, in embodiments in which the outer crotch edge 80 follows an arcuate path, the inward fin crotch seam 60 can follow a corresponding arcuate path. It should be noted that the inward fin crotch seam 60 can follow a path which is straight, arcuate, or any combination of one or more straight and/or arcuate segments between leg sleeves 110. FIGS. 1–4 representatively illustrate inward fin crotch seams 60 which follow an arcuate path generally concave in shape relative to the waist edges 42 and 44. FIG. 5 representatively illustrates an inward fin crotch seam 60 following a generally straight path. FIGS. 8 and 9 representatively illustrate inward fin crotch seams 60 which follow a arcuate path generally convex in shape relative to the waist edges 42 and 44.

As representatively illustrated in FIG. 1, the inward fin crotch seam 60 can have one or more slits 62 which divide the crotch seam 60 into two or more crotch seam sections 64. The slits 62 can provide flexibility to the crotch seam 60. Additionally, the slits can allow the inward fin crotch seam 60 to "fan out" into two or more crotch seam sections 64 if the crotch seam is initially made while the disposable pant 30 is in an "inside-out" configuration, as will be more fully explained below. The inward fin crotch seam 60 can have any number of slits, such as, for example, one or more slits, particularly between two and four slits per inch of crotch seam edge 67. The slits 62 can but need not fully penetrate both panels 40 and 42.

Figure 3:
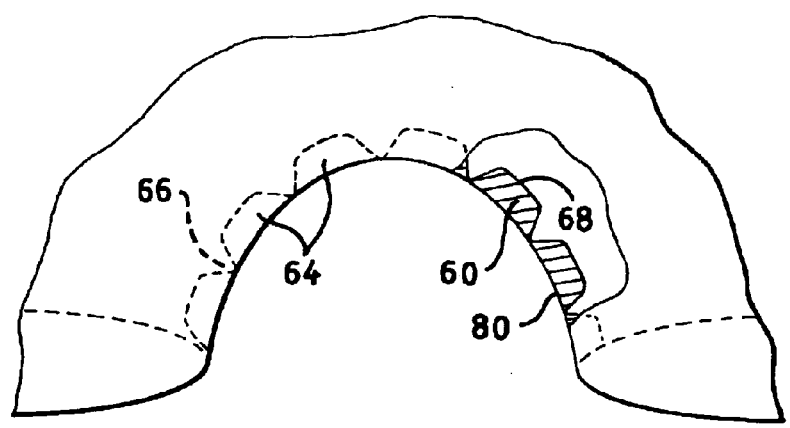
FIG. 3 is an enlarged view of a region of an alternative embodiment of the disposable pant of FIG. 1, with portions cut away to show the underlying features.
Figure 4:
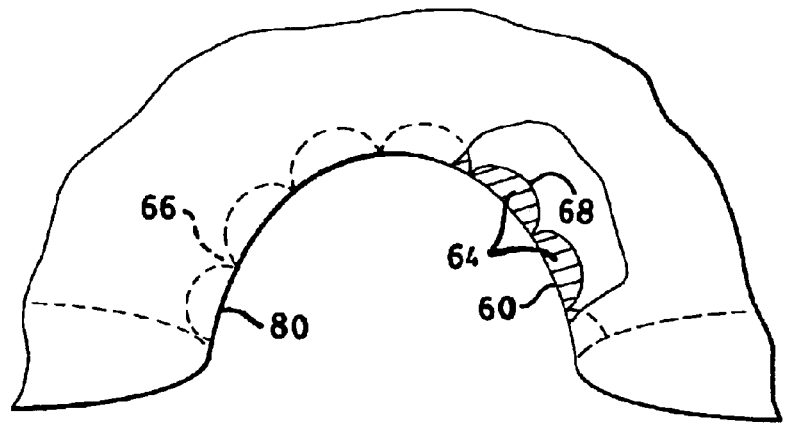
FIG. 4 is an enlarged view of a region of an alternative embodiment of the disposable pant of FIG. 1, with portions cut away to show the underlying features.
Figure 5:
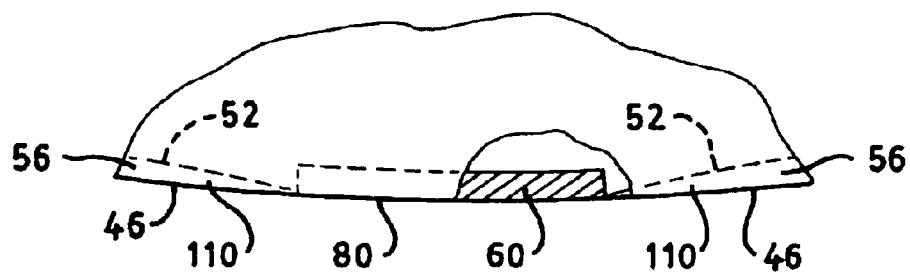
FIG. 5 is an enlarged view of a region of an alternative embodiment of the disposable pant of FIG. 1, with portions cut away to show the underlying features.
Figure 6:
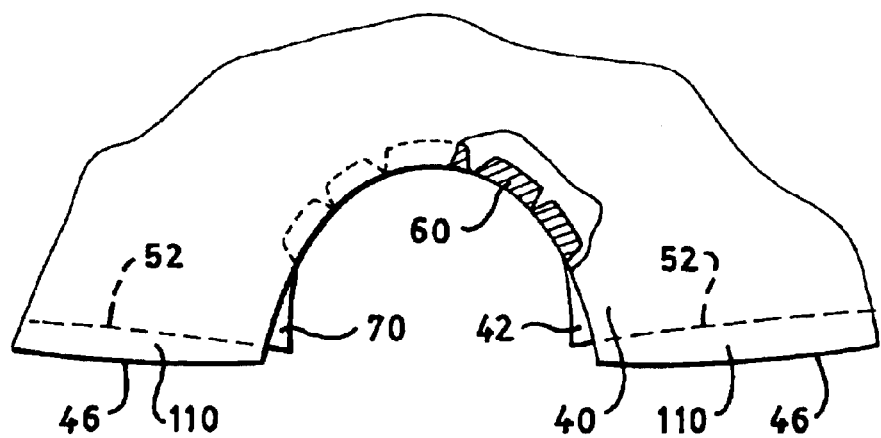
FIG. 6 is an enlarged view of a region of an alternative embodiment of the disposable pant of FIG. 1, with portions cut away to show the underlying features.

Alternatively, the inward fin crotch seam 60 can have one or more notches 66 which divide the crotch seam 60 into two or more crotch seam sections 64, as representatively illustrated in FIGS. 3 and 4. The term "notch" as used herein refers to a section of material that has been cutout and removed. Similar to the slits 62 mentioned above, the notches 66 can provide flexibility to the crotch seam 60, and can allow the inward fin crotch seam 60 to "fan out" into two or more crotch seam sections 64 following "inside-out" manufacture, explained below. Further, notches 66 can produce crotch seam section edges 68 having less pointed corners or no corners. For example, an inward fin crotch seam 60 having notches 66 as representatively illustrated in FIG. 3 has crotch seam section edges 68 having obtuse corners. In another embodiment, as representatively illustrated in FIG. 4, the crotch seam 60 has arcuate crotch seam section edges 68. Crotch seam section edges 68 such as those depicted in FIGS. 3 and 4 can be more comfortable against the skin of a wearer. In yet another embodiment, as representatively illustrated in FIGS. 8 and 9, the crotch seam 60 has notches 66 which allow the inward fin crotch seam 60 to "fan in" following "inside-out" manufacture, explained below. The inward fin crotch seam 60 can have any number of notches, such as, for example, one or more notches, particularly between one and three notches per inch of crotch seam edge 67. The notches 66 can but need not fully penetrate both panels 40 and 42.

The crotch seam 60 may or may not intersect the panel leg edges 46 and 52. For example, as representatively illustrated in FIG. 1, the crotch seam 60 may intersect the panel leg edges 46 and 52. Alternatively, as representatively illustrated in FIG. 6, the crotch seam 60 may be spaced remotely from the leg edges 46 and 52, leaving an unbonded leg sleeve area 70. In such an embodiment, the first panel 40 and the second panel 42 remain unconnected to each other in the unbonded leg sleeve area 70 between the crotch seam 60 and/or the panel leg edges 46 or 52. The unbonded area can deliver a more comfortable fit to the wearer, allowing the leg sleeves 110 to expand about the thigh.

Figure 7:
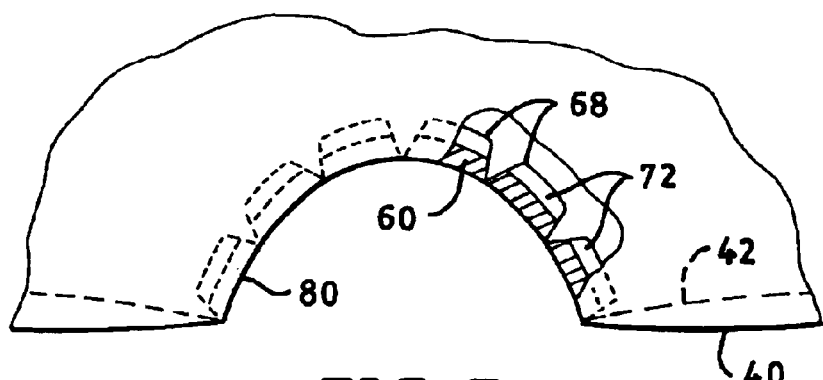
FIG. 7 is an enlarged view of a region of an alternative embodiment of the disposable pant of FIG. 1, with portions cut away to show the underlying features.

Referring to FIGS. 7 and 9, the inward fin crotch seam 60 can include an unbonded crotch seam area 72. For example, panels 40 and 42 can remain unconnected to each other in the unbonded crotch seam area 72 which abuts at least a part of one or more crotch seam section edges 68 or which abuts at least part of a single crotch seam edge if the crotch seam is not split into multiple sections. The unbonded crotch seam area 72 can result in a softer and more comfortable surface against the skin of the wearer, as the portion of the inward fin crotch seam 60 most likely to touch the skin of the wearer will be unbonded and relatively pliant, versus a stiffer seam which might be produced if the panels 40 and 42 were bonded together along the crotch seam section edges 68.

Figure 10:
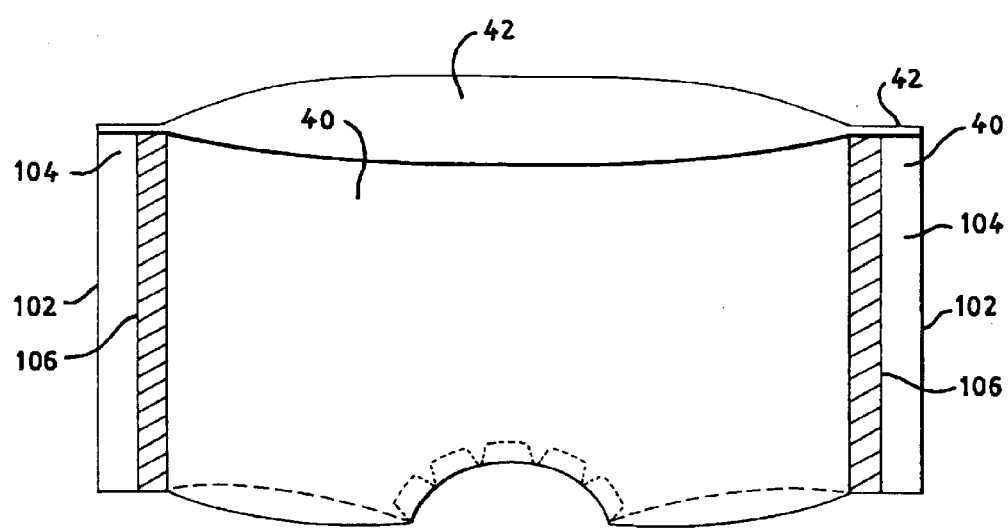
FIG. 10 is a perspective view of an alternative embodiment of the disposable pant according to the present invention.

The disposable pant 30 also includes side regions 90 and side seams 100. As representatively illustrated in FIG. 1, the side seams 100 connect the side regions 90 of the first panel 40 to the side regions 90 of the second panel 42 to create the disposable pant 30. The cross-hatching within the side seams 100 in the Figures denotes a region in which the first panel 40 and second panel 42 are bonded to one another. The side seams 100 can take any number of forms, including both refastenable and non-refastenable seams. For example, the side seams 100 can be outward fin seams, as representatively illustrated in FIG. 1. Alternatively, the side seams 100 can be inward fin seams or lap seams (not shown). In addition, the side seams 100 may or may not abut the side edges 102. For example, as representatively illustrated in FIG. 1, the side seams 100 can abut the pant side edges 102. Alternatively, as representatively illustrated in FIG. 10, at least a portion 104 of the first panel 40 remains unbonded to the second panel 42 between an outer edge 106 of at least one side seam and the nearest side edge 102. Such a design can result in a disposable pant 30 having relatively soft, pliant side edges 102.

The disposable pant 30 can also include an absorbent structure 138. For example, as representatively illustrated in FIG. 1, the absorbent structure can take the form of two absorbent panels 140 and 142. Specifically, the disposable pant 30 can have a first absorbent panel 140 attached to or integral with the first panel 40, and a second absorbent panel 142 attached to or integral with the second panel 42. In particular embodiments, the absorbent panels are centrally located in the pant relative to the pant's longitudinal dimension 34. Such positioning can allow the absorbent panels 140 and 142 to efficiently absorb liquid body waste in the crotch region of the garment. It should be noted that the disposable pant 30 need not include multiple absorbent panels. For example, the disposable pant 30 can include only one absorbent panel located in the front of the garment, such as absorbent panel 140.

In particular embodiments, the disposable pant 30 includes absorbent panels contained within, or integral with, the first and/or second panels 40 and 42. For example, as representatively illustrated in FIGS. 1 and 11, absorbent panels 140 and 142 can be contained within the panels 40 and 42, such as by being sandwiched between an outer cover 41 and a liner 43. In another embodiment, representatively illustrated in FIGS. 12 and 13, the absorbent panels 140 and 142 can be positioned upon the inner surface 45 of the panels 40 and 42. In such an embodiment, the absorbent panels are desirably contained within an absorbent wrap 158. The absorbent wrap 158 is desirably constructed of a liquid-permeable material such as that used in the construction of a pant liner, described below.

In particular embodiments, the absorbent panels 140 can be provided in a manner such that they shield the wearer from the inward fin crotch seam 60. For example, as representatively illustrated in FIGS. 11 and 13, the inward fin crotch seam can protrude into the interior of the garment and thus has the potential of causing discomfort for the wearer. As representatively illustrated in FIG. 11, the absorbent panels 140 and 142 can have a thickness 150 in a region 152 near the inward fin crotch seam 60 that is greater than the height 61 of the crotch seam 60, such that the inward fin crotch seam 60 is recessed relative to the inner surface 154 of the absorbent panels 140 and 142. In particular embodiments, absorbent panels 140 and 142 have a thickness 150 in the region 152 near the inward fin crotch seam 60 which exceeds the height 61 of the crotch seam by at least about one millimeter, more particularly from about two millimeters to about and 20 millimeters, and still more particularly from about three millimeters to about 10 millimeters. In such embodiments, the absorbent panels 140 and 142 can have such a thickness 150 only in the region 152 near the inward fin crotch seam, or can have such a thickness 150 over its entire area. In particular embodiments, the absorbent panels 140 and 142 can have an increased thickness in regions 152 relative to other areas of the absorbent panels to improve the absorbency and/or comfort of the disposable pant 30 in the crotch region 55.

Figure 12:
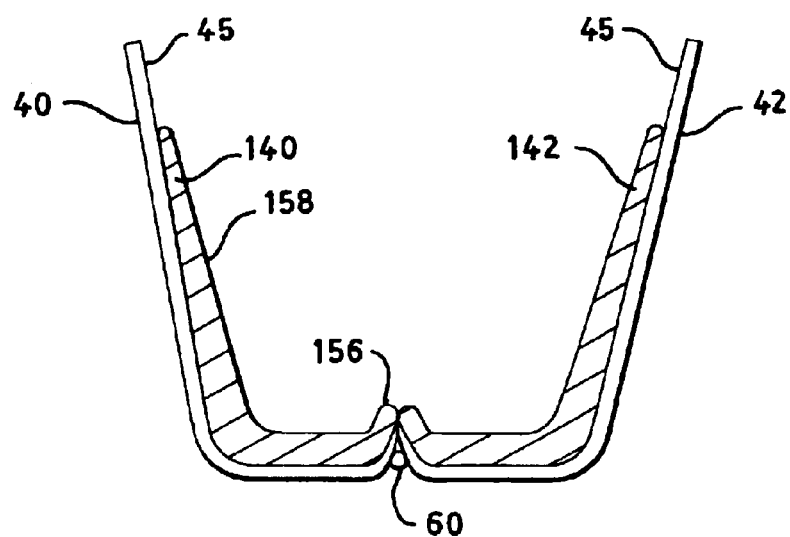
FIG. 12 is a section view of an alternative embodiment of the pant of FIG. 1 taken from the plane of line 25—25 in FIG. 1.
Figure 13:
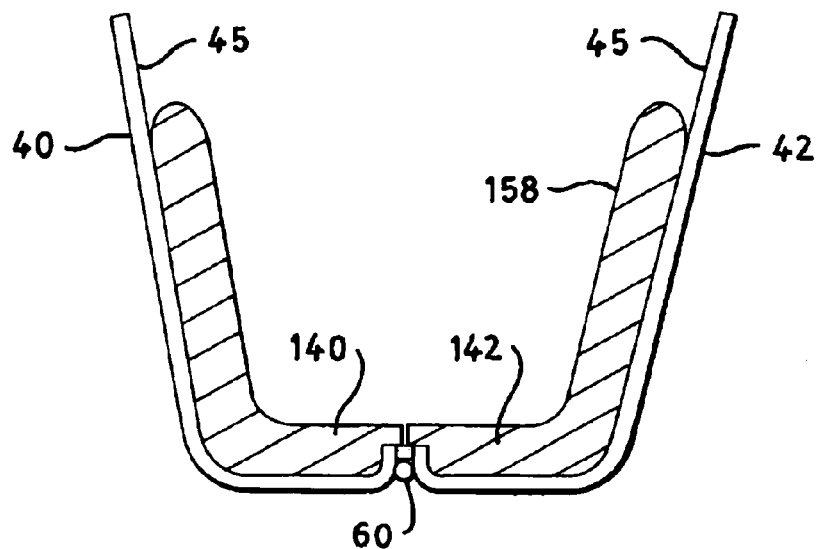
FIG. 13 is a section view of an alternative embodiment of the pant of FIG. 1 taken from the plane of line 25—25 in FIG. 1.

In another embodiment, the absorbent panels 140 and 142 can be positioned to cover the inward fin crotch seam 60, as representatively illustrated in FIGS. 12 and 13. For example, the absorbent panels 140 and 142 can be positioned on the inner surface 45 of the panels 40 and 42, such the absorbent panel crotch ends 156 contact each other when the disposable pant 30 is being worn. Such a design can shield the wearer from the inward fin crotch seam 60 during use. In particular embodiments, such as that representatively illustrated in FIG. 13, the absorbent panels 140 and 142 are shaped to accommodate the inward fin crotch seam 60 to deliver a flat, smooth surface to the wearer in the crotch region 55 of the pant 30.

The absorbent structure need not take the form of two separate panels as heretofore described. Instead, in particular embodiments, the disposable pant 30 can include a single absorbent panel 170 as representatively illustrated in FIG.

14. For example, a single absorbent panel 170 can be attached to the first panel 40 and the second panel 42, and can cover at least part of the inward fin crotch seam 60. The single absorbent panel 170 can, but need not, contact the inward fin crotch seam 60. The single absorbent panel 170 may or may not include an indentation 172 to accommodate the inward fin crotch seam 60, thus potentially delivering a flat, smooth surface to the wearer in the crotch region 55 of the pant 30.

The absorbent panels 140 and/or 142 and the single absorbent panel 170 can be sized to meet various performance, manufacturing, or cost constraints. For example, absorbent panel 140 can have dimensions similar to the first panel 40, or can, alternatively, be relatively concentrated near the longitudinal center of the pant 30, as representatively illustrated in FIG. 1. Moreover, the absorbent panels 140 and 142 can be longitudinally centered or skewed forward or backward in the pant 30.

The first and second panels 40 and 42 are desirably constructed of materials which are comfortable against the skin and non-irritating. For example, as representatively illustrated in FIG. 11, the panels 40 and 42 may include an outer cover 41 and a liner 43. The outer cover 41 can, but need not, comprise a material that is substantially liquid impermeable, and can be elastic, stretchable, or nonstretchable. The outer cover 41 can be a single layer of liquid impermeable material, but desirably comprises a multi-layered laminate structure in which at least one of the layers is liquid impermeable. For instance, the outer cover 41 can include a liquid permeable outer layer and a liquid impermeable inner layer that are suitably joined together by a laminate adhesive, ultrasonic bonds, thermal bonds, or the like. Suitable laminate adhesives, which can be applied continuously or intermittently as beads, a spray, parallel swirls, or the like, can be obtained from Findley Adhesives, Inc., of Wauwatosa, Wis. U.S.A., or from National Starch and Chemical Company, Bridgewater, N.J. U.S.A. The liquid permeable outer layer can be any suitable material and desirably one that provides a generally cloth-like texture. One example of such a material is a 20 gsm (grams per square meter) spunbond polypropylene nonwoven web. The outer layer may also be made of those materials of which liquid permeable bodyside liner 43 is made. While it is not a necessity for outer layer to be liquid permeable, it is desired that it provides a relatively cloth-like texture to the wearer.

The inner layer of the outer cover 41 can be both liquid and vapor impermeable, or can be liquid impermeable and vapor permeable. The inner layer can be manufactured from a thin plastic film, although other flexible liquid impermeable materials may also be used. The inner layer, or the liquid impermeable outer cover 41 when a single layer, prevents waste material from wetting articles, such as bedsheets and clothing, as well as the wearer and caregiver. A suitable liquid impermeable film for use as a liquid impermeable inner layer, or a single layer liquid impermeable outer cover 41, is a 0.02 millimeter polyethylene film commercially available from Huntsman Packaging of Newport News, Va. U.S.A. If the outer cover 41 is a single layer of material, it can be embossed and/or matte finished to provide a more cloth-like appearance. As earlier mentioned, the liquid impermeable material can permit vapors to escape from the interior of the disposable absorbent article, while still preventing liquids from passing through the outer cover 41. A suitable "breathable" material is composed of a microporous polymer film or a nonwoven fabric that has been coated or otherwise treated to impart a desired level of liquid impermeability. A suitable microporous film is a PMP-1 film material commercially available from Mitsui Toatsu Chemicals, Inc., Tokyo, Japan, or an XKO-8044 polyolefin film commercially available from 3M Company, Minneapolis, Minn. U.S.A.

The bodyside liner 43 is desirably compliant, soft feeling, and non-irritating to the skin. Further, the bodyside liner 43 can be less hydrophilic than the absorbent structure 138 to present a relatively dry surface to the wearer and permit liquid to readily penetrate through its thickness. Alternatively, the bodyside liner 43 can be more hydrophilic or can have essentially the same affinity for moisture as the absorbent structure 138 to present a relatively wet surface to the wearer to increase the sensation of being wet. This wet sensation can be useful as a toilet training aid. The hydrophilic/hydrophobic properties can be varied across the length, width and depth of the bodyside liner 43 to achieve the desired wetness sensation or leakage performance.

The bodyside liner 43 can be manufactured from a wide selection of web materials, such as synthetic fibers (for example, polyester or polypropylene fibers), natural fibers (for example, wood or cotton fibers), a combination of natural and synthetic fibers, porous foams, reticulated foams, apertured plastic films, or the like. Various woven and nonwoven fabrics can be used for the bodyside liner 43. For example, the bodyside liner can be composed of a meltblown or spunbonded web of polyolefin fibers. The bodyside liner can also be a bonded-carded web composed of natural and/or synthetic fibers. The bodyside liner can be composed of a substantially hydrophobic material, and the hydrophobic material can, optionally, be treated with a surfactant or otherwise processed to impart a desired level of wettability and hydrophilicity. For example, the material can be surface treated with about 0.45 weight percent of a surfactant mixture comprising Ahcovel N-62 from Hodgson Textile Chemicals of Mount Holly, N.C. U.S.A. and Glucopan 220UP from Henkel Corporation of Ambler, Pa. in an active ratio of 3:1. The surfactant can be applied by any conventional means, such as spraying, printing, brush coating or the like. The surfactant can be applied to the entire bodyside liner 43 or can be selectively applied to particular sections of the bodyside liner, such as the medial section along the longitudinal center line.

A suitable liquid permeable bodyside liner 43 is a nonwoven bicomponent web having a basis weight of about 27 gsm. The nonwoven bicomponent can be a spunbond bicomponent web, or a bonded carded bicomponent web. Suitable bicomponent staple fibers include a polyethylene/polypropylene bicomponent fiber available from CHISSO Corporation, Osaka, Japan. In this particular bicomponent fiber, the polypropylene forms the core and the polyethylene forms the sheath of the fiber. Other fiber orientations are possible, such as multi-lobe, side-by-side, end-to-end, or the like. The outer cover 41, bodyside liner 43 and other materials used to construct the pant can comprise elastomeric or nonelastomeric materials.

Each of the panels 40 and 42 can include one or more individual, distinct pieces of material. The panels 40 and 42 desirably although not necessarily comprise a stretchable or elastic material capable of stretching in one or more directions, and in particular embodiments are stretchable or elastic in a direction generally parallel to the panel waist edges 44 and 50. Suitable elastic materials are described in the following U.S. Pat. No. 4,940,464 issued Jul. 10, 1990 to Van Gompel et al.; U.S. Pat. No. 5,224,405 issued Jul. 6, 1993 to Pohjola; U.S. Pat. No. 5,104,116 issued Apr. 14, 1992 to Pohjola; and U.S. Pat. No. 5,046,272 issued Sep. 10, 1991 to Vogt et al.; all of which are incorporated herein by reference to the extent they are not inconsistent herewith. In particular embodiments, the elastic material comprises a stretch-thermal laminate (STL), a neck-bonded laminate (NBL), a reversibly necked laminate, or a stretch-bonded laminate (SBL) material. Methods of making such materials are well known to those skilled in the art and described in U.S. Pat. No. 4,663,220 issued May 5, 1987 to Wisneski et al.; U.S. Pat. No. 5,226,992 issued Jul. 13, 1993 to Morman; and European Patent Application No. EP 0 217 032 published on Apr. 8, 1987 in the names of Taylor et al.; all of which are incorporated herein by reference. Alternatively, the panels 40 and 42 may comprise other woven or nonwoven materials, such as mechanically pre-strained composites, or stretchable but inelastic materials.

The absorbent structure 138 can be any structure which is generally compressible, conformable, non-irritating to the skin, and capable of absorbing and retaining liquids and certain body wastes. The absorbent structure 138 can be manufactured in a wide variety of sizes and shapes, from a wide variety of liquid absorbent materials commonly used in the art, and may be stretchable, non-stretchable, or elastic. For example, the absorbent structure 138 can suitably comprise a matrix of hydrophilic fibers, such as a web of cellulosic fluff, mixed with particles of a high-absorbency material commonly known as superabsorbent material. In a particular embodiment, the absorbent structure 138 comprises a matrix of cellulosic fluff, such as wood pulp fluff, and superabsorbent hydrogel-forming particles. The wood pulp fluff can be exchanged with synthetic, polymeric, meltblown fibers or short cut homofil bicomponent synthetic fibers and natural fibers. The superabsorbent particles can be substantially homogeneously mixed with the hydrophilic fibers or can be nonuniformly mixed. The fluff and superabsorbent particles can also be selectively placed into desired zones of the absorbent structure 138 to better contain and absorb body exudates. The concentration of the superabsorbent particles can also vary through the thickness of the absorbent structure 138. Alternatively, the absorbent strucutre 138 can comprise a laminate of fibrous webs and superabsorbent material or other suitable means of maintaining a superabsorbent material in a localized area.

Suitable superabsorbent materials can be selected from natural, synthetic, and modified natural polymers and materials. The superabsorbent materials can be inorganic materials, such as silica gels, or organic compounds, such as crosslinked polymers, for example, sodium neutralized polyacrylic acid. Suitable superabsorbent materials are available from various commercial vendors, such as Dow Chemical Company located in Midland, Mich. U.S.A., and Stockhausen GmbH & Co. KG, D-47805 Krefeld, Federal Republic of Germany. Typically, a superabsorbent material is capable of absorbing at least about 15 times its weight in water, and desirably is capable of absorbing more than about 25 times its weight in water.

In one embodiment, the absorbent structure 138 comprises a blend of wood pulp fluff and superabsorbent material. One preferred type of pulp is identified with the trade designation CR1654, available from U.S. Alliance, Childersburg, Ala. U.S.A., and is a bleached, highly absorbent sulfate wood pulp containing primarily soft wood fibers and about 16 percent hardwood fibers. As a general rule, the superabsorbent material is present in the absorbent structure 138 in an amount of from 0 to about 90 weight percent based on total weight of the absorbent assembly. The absorbent structure 138 suitably has a density within the range of about 0.10 to about 0.35 grams per cubic centimeter. The absorbent structure 138 may or may not be wrapped or encompassed by a suitable tissue wrap that may help maintain the integrity and/or shape of the absorbent assembly.

The absorbent structure 138 can also incorporate other materials that are designed primarily to receive, temporarily store, and/or transport liquid along the mutually facing surface with absorbent structure 138, thereby maximizing the absorbent capacity of the absorbent assembly. One suitable material is referred to as a surge layer (not shown) and comprises a material having a basis weight of about 50 to about 120 grams per square meter, and comprising a through-air-bonded-carded web of a homogenous blend of 60 percent 3 denier type T-256 bicomponent fiber comprising a polyester core/polyethylene sheath and 40 percent 6 denier type T-295 polyester fiber, both commercially available from Kosa Corporation of Salisbury, N.C. U.S.A.

In particular embodiments, the absorbent structure 138 is thin to provide a slim, comfortable, non-bulky disposable pant 30. Any suitable thin absorbent structure may be used. For example, the absorbent structure 138 may be constructed of an absorbent nonwoven fabric, such as that described in U.S. Pat. No. 4,100,324, issued Jul. 17, 1978 to Anderson et al., which is incorporated herein by reference. In particular embodiments, the absorbent structure 138 can include meltblown KRATON® elastic polymer, available from Kraton Polymers U.S. LLC of Houston, Tex., U.S.A.

The present invention also includes various methods for making disposable pants having inward fin crotch seams, as shall now be explained and illustrated. Referring to FIGS. 15a–15f, first panel 40 and second panel 42, each of which has an inner surface 120 and an outer surface 122, are positioned such that their outer surfaces 122 are in a facing relationship. The panels 40 and 42 are connected to one another along a crotch seam 160, as shown in FIG. 15b. After the crotch seam 160 is made, the panels 40 and 42 are repositioned (FIG. 15d) such that their inner surfaces 120 are in a facing relationship as shown in FIG. 15e. At this point, as can be seen in FIG. 15e, the crotch seam 160 can be sandwiched between panels 40 and 42. Finally, panels 40 and 42 are connected at their side regions 90 to form side seams 100, creating a disposable pant 30 having a waist opening 54 and two leg openings 56.

Figure 16A:
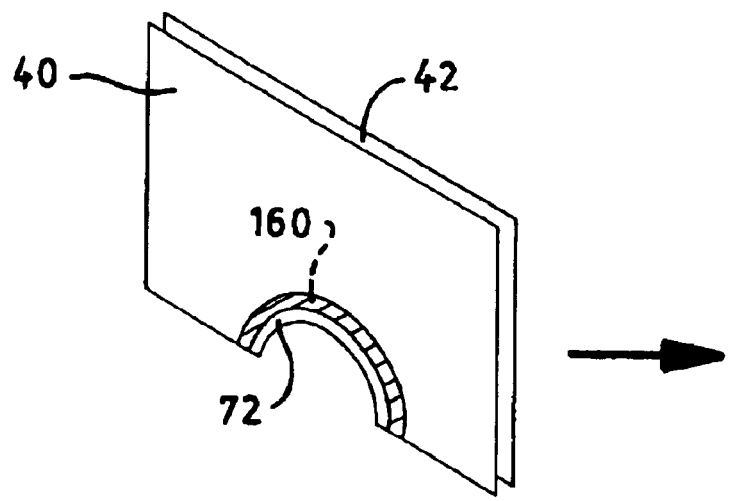
FIGS. 16a–b are perspective views of two stages of an alternative embodiment of the method according to the present invention.
Figure 16B:
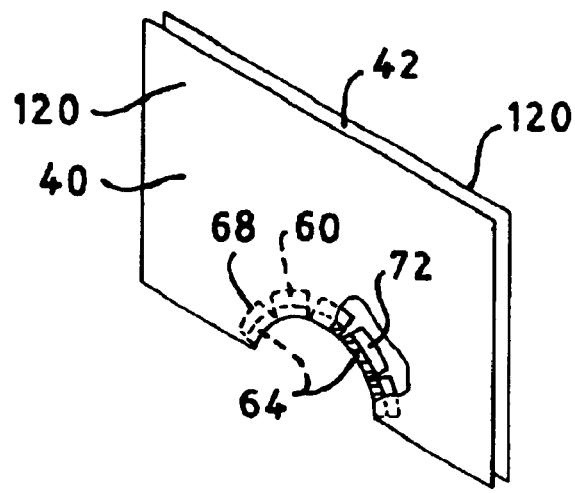

A variety of alterations or additions to this basic method may be contemplated. For example, following the creation of the crotch seam 160, but preferably before the panels 40 and 42 are repositioned as described above, a section of material 162 can be removed from either or both panels in the area between the crotch seam 160 and the panel leg edges 46 to define an outer crotch edge 80, as representatively shown in FIG. 15b. In another variation, following the creation of the crotch seam 160, but preferably before the panels 40 and 42 are repositioned as described above, notches 66 may be cut from the crotch seam 160, as representatively shown in FIG. 15c. As explained earlier, notches 66 allow the crotch seam 160 to "fan apart" when the panels 40 and 42 are reoriented, as shown in FIG. 15e. Alternatively, slits may be cut into the crotch seam 160. In yet another variation, the panels 40 and 42 are connected to one another along a crotch seam 160, but remain unconnected to one another along an unbonded crotch seam area 72, representatively illustrated in FIG. 16a. When the panels 40 and 42 are repositioned such that their inner surfaces 120 are in a facing relationship as shown in FIG. 16b, the unbonded crotch seam area 72 can result in a softer and more comfortable surface against the skin of the wearer, as the portion of the inward fin crotch seam 60 most likely to touch the skin of the wearer will be unbonded and relatively pliant, versus a stiffer seam which might be produced if the panels 40 and 42 were bonded together along the crotch seam section edges 68. Many other alterations and additions will be readily appreciated by those skilled in the art, including the formation of arched leg openings (FIG. 8).

Figure 17:
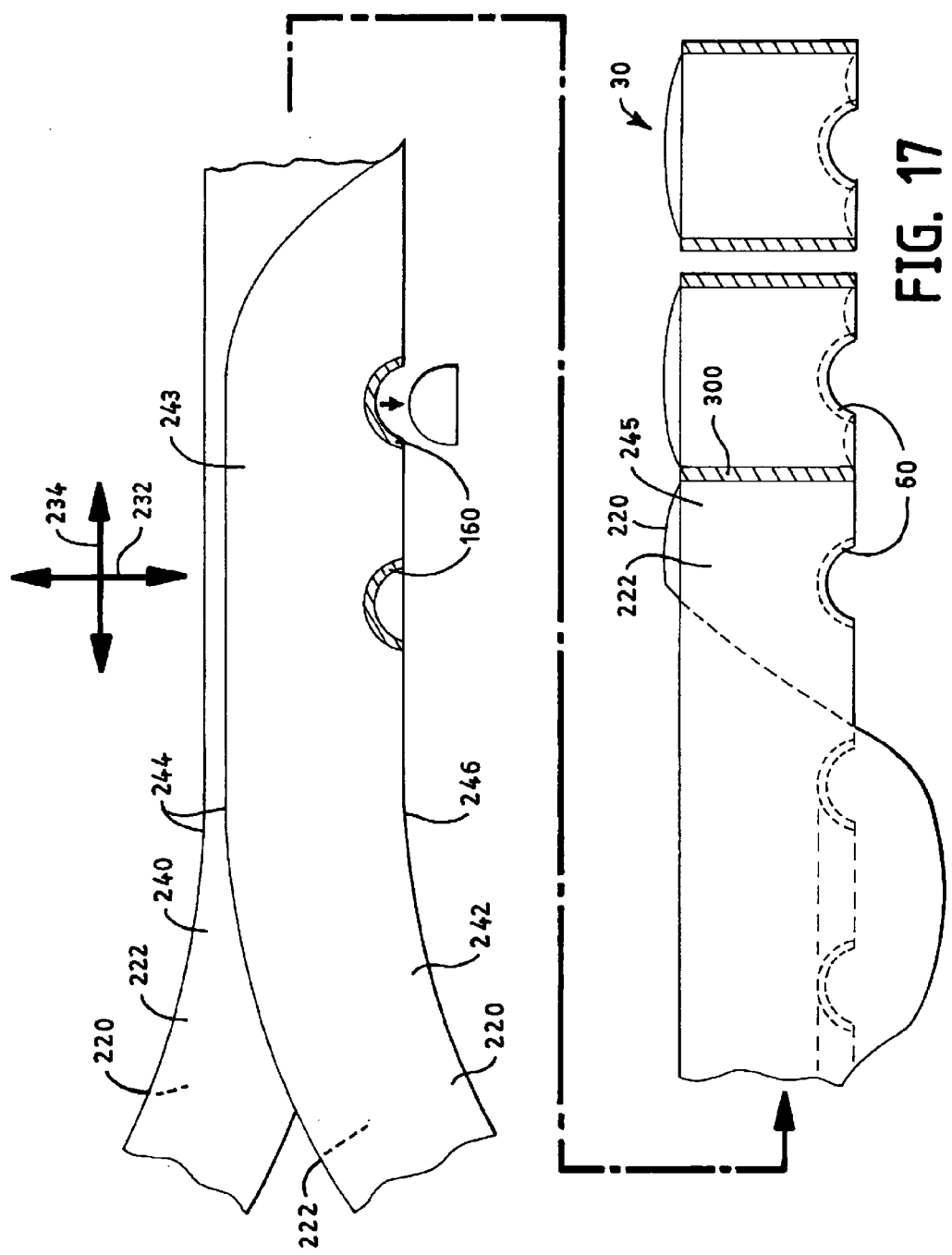
FIG. 17 is a schematic view of one embodiment of the method according to the present invention, split into two partial views.

FIG. 17 representatively illustrates one embodiment of a method of the present invention for making a continuous stream of disposable pants having inward crotch seams. A particular embodiment involves providing a first web 240 and a second web 242, each web having a transverse direction 232 and a longitudinal direction 234, an inner surface 220, an outer surface 222, a web waist edge 244 generally aligned with the longitudinal direction 234, and a web leg edge 246 generally aligned with the longitudinal direction 234. The webs 240 and 242 can have the same transverse width, or may differ in transverse width. The webs 240 and 242 are positioned such that their outer surfaces 222 are in a facing relationship. In particular embodiments, the webs 240 and 242 are equal in transverse width and are positioned such that their web waist edges 244 and web leg edges 246 coincide, as representatively illustrated in FIG. 16. Alternatively, the webs 240 and 242 can have different transverse widths, in which case it may be preferable to have the web waist edges 244 coincide. Additionally, the web waist edges 244 and/or web leg edges 246 may be folded if desired to form waist and/or leg cuffs 112 and 114 (FIG. 1), which may or may not include elastic members (not shown).

The webs are bonded together at a plurality of locations in the longitudinal direction 234 to define a plurality of crotch seams 160, creating an "inside-out" composite pant web 243. The crotch seams may but need not be inset from one or both web leg edges 246. The first and second webs 240 and 242 are then repositioned such that their inner surfaces 220 are in a facing relationship, creating an "outside-out" composite pant web 245 having a plurality of inward fin crotch seams 60 spaced apart in the longitudinal direction 234. The first and second webs 240 and 242 are then bonded together at a plurality of locations in the longitudinal direction 234 to define a plurality of web side seams 300, each web side seam positioned longitudinally between a pair of inward fin crotch seams 60. The outside-out composite pant web 245 is cut into a plurality of disposable pants 30, each disposable pant having a waist opening 54, two leg openings 56, two pant side seams 100, and an inward fin crotch seam 60.

Figure 18:
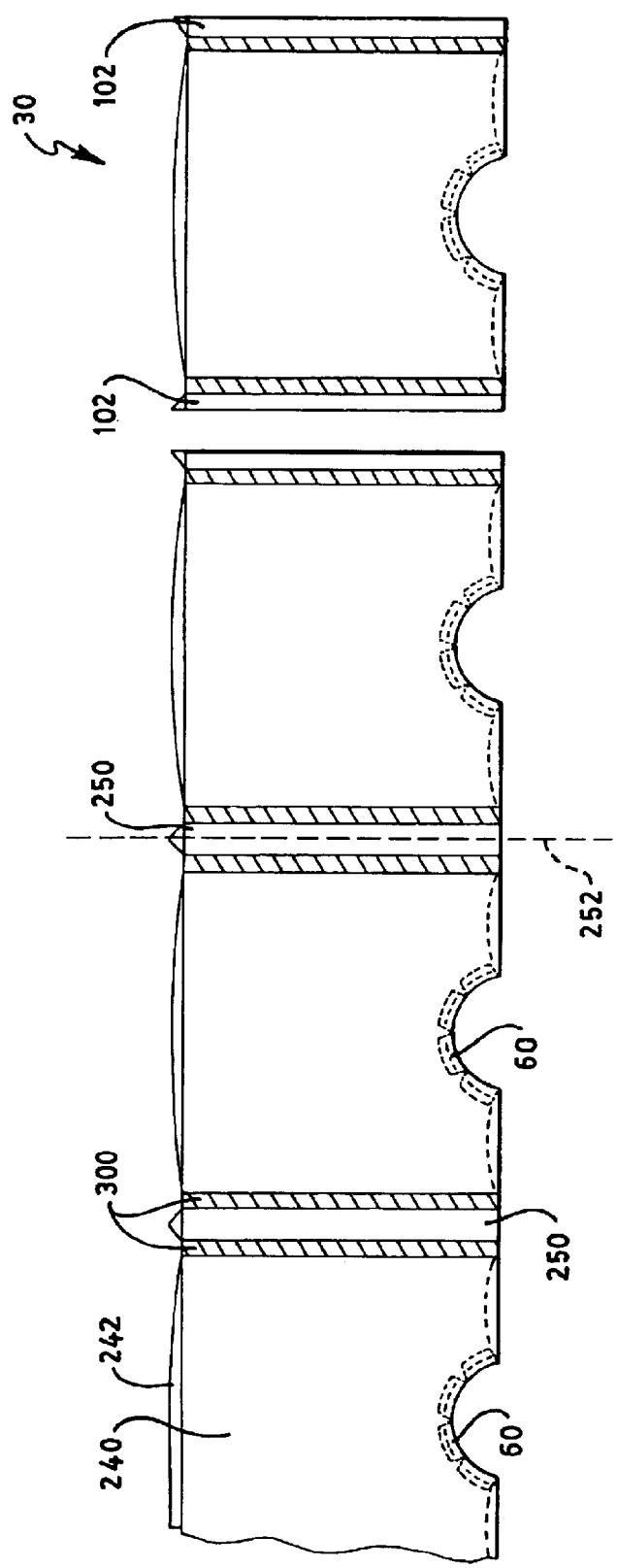
FIG. 18 is a schematic view of a portion of an alternative embodiment of the method according to the present invention.

As representatively illustrated in FIG. 18, one particular embodiment of a method of the present invention involves bonding two web side seams 300 longitudinally between each pair of inward fin crotch seams 60, such that the first web 240 and second web 242 remain substantially unbonded in the area 250 longitudinally between the two web side seams 300. The outside-out composite pant web 245 can be cut into a plurality of disposable pants 30 along a cut line 252 in the unbonded area 250. This particular embodiment of the method can result in disposable pants 30 having relatively soft, pliant side edges 102. The web side seams (FIGS. 17 and 18) can comprise permanently bonded seams or refastenable seams.

In particular embodiments, an absorbent structure 138 is included in the disposable pant 30. The absorbent structure 138 can be introduced into the pant 30 in any suitable manner. For example, absorbent panels may be integral with the first web 240 and/or the second web 242 such that the resulting disposable pants 30 each contain one or more absorbent panels. In another embodiment, absorbent panels can be placed against the inner surface 220 of one or both webs 240 and 242. For example, in one particular embodiment, absorbent panels 140 and 142 can be placed against the inner surfaces 220 of the first and second webs 240 and 242 following creation of a crotch seam 160 and removal of a section of material 162. The absorbents panels 140 and 142 can, but need not, extend transversely past the outer crotch edge 280. In particular embodiments, the absorbent panels 140 and 142 extend transversely past the outer crotch edge 280 such that when the webs are repositioned and converted to disposable pants 30 as described above, the absorbent panels 140 and 142 contact each other in the vicinity of the crotch region 55 of the disposable pant 30, thus enhancing the absorbency and comfort of the pant.

The various components of the disposable pant can be connected together by any means known to those skilled in the art such as, for example, adhesive, thermal and/or ultrasonic bonds. Desirably, most of the components are connected using ultrasonic bonding for improved manufacturing efficiency and reduced raw material costs. For example, in particular embodiments, the crotch seam 160 and the side seams 100 are made using ultrasonic bonding. Certain garment manufacturing equipment which is readily known and understood in the art, including frames and mounting structures, ultrasonic and adhesive bonding devices, transport conveyors, transfer rolls, guide rolls, tension rolls, and the like, have not been shown in the Figures.

It will be appreciated that details of the foregoing embodiments, given for purposes of illustration, are not to be construed as limiting the scope of this invention. Although only a few exemplary embodiments of this invention have been described in detail above, those skilled in the art will readily appreciate that many modifications are possible in the exemplary embodiments without materially departing from the novel teachings and advantages of this invention. For example, features described in relation to one embodiment may be incorporated into any other embodiment of the invention. Accordingly, all such modifications are intended to be included within the scope of this invention, which is defined in the following claims and all equivalents thereto. Further, it is recognized that many embodiments may be conceived that do not achieve all of the advantages of some embodiments, particularly of the preferred embodiments, yet the absence of a particular advantage shall not be construed to necessarily mean that such an embodiment is outside the scope of the present invention.

What is claimed is:

1. A method of making a disposable pant having an inward fin crotch seam, comprising:
   providing first and second panels, each panel having an inner surface, an outer surface, a panel waist edge, a panel leg edge, and two side regions;
   positioning the panels such that their respective outer surfaces are in a facing relationship;
   bonding the panels together to form a crotch seam;
   repositioning the panels such that the inner surfaces are in a facing relationship; and
   bonding the side regions of the first panel to the side regions of the second panel to create two side seams to define a waist opening and two leg openings;
   wherein the side seams are fin seams; and
   wherein the pant has two side edges, and at least a portion of the first panel remains unbonded to the second panel between an outer edge of at least one side seam and the nearest side edge.

2. A method of making a disposable pant having an inward fin crotch seam, comprising:

providing first and second panels, each panel having an inner surface, an outer surface, a panel waist edge, a panel leg edge, and two side regions;

positioning the panels such that their respective outer surfaces are in a facing relationship;

bonding the panels together to form a crotch seam;

repositioning the panels such that the inner surfaces are in a facing relationship; and bonding the side regions of the first panel to the side regions of the second panel to create two side seams to define a waist openings and two leg openings; and wherein each side seam extends less than the entire distance from the waist opening to the nearest leg opening.

3. A method of making a disposable pant having an inward fin crotch seam, comprising:

providing first and second panels, each panel having an inner surface, an outer surface, a panel waist edge, a panel leg edge, and two side regions;

positioning the panels such that their respective outer surfaces are in a facing relationship;

bonding the panels together remote from the panel leg edges to form an inset crotch seam;

removing sections of the panels between the inset crotch seam and the panel leg edges to define an outer crotch edge;

repositioning the panels such that the inner surfaces are in a facing relationship; and bonding the side region of the first panel to the side regions of the second panel to create two side seams to define a waist opening and two leg openings.

4. The method of claim 3 wherein the outer crotch edge is arcuate.

5. The method of claim 3 wherein the first panel remains unbonded to the second panel in at least a portion of an area between the inset crotch seam and the outer crotch edge.

6. The method of claim 3 wherein the inset crotch seam does not intersect either panel leg edge.

7. A method of making a disposable pant having an inward crotch seam, comprising:

providing first and second panels, each panel having an inner surface, an outer surface, a panel waist edge, a panel leg edge, and two side regions;

positioning the panels such that their respective outer surfaces are in a facing relationship;

bonding the panels together to form a crotch seam having an crotch seam edge;

cutting at least one slit in the crotch seam to define at least two crotch seam sections, each section having a crotch seam section edge;

repositioning the panels such that the inner surfaces are in a facing relationship; and bonding the side regions of the first panel to the side regions of the second panel to create two side seams to define a waist opening and two leg openings.

8. The method of claim 7 having at least five slits.

9. The method of claim 7 wherein the cutting step includes cutting notches in the crotch seam.

10. The method of claim 9 wherein at least a part of each crotch seam section edge is arcuate.

11. The method of claim 7 wherein each slit is generally perpendicular to the crotch seam edge.

12. The method of claim 7 wherein each slit passes completely through each panel.

13. A method of making disposable pants having inward crotch seams, comprising:

providing first and second webs, each web having a longitudinal direction, a transverse direction, an inner surface, an outer surface, a web waist edge generally aligned with the longitudinal direction, and a web leg edge generally aligned with the longitudinal direction;

positioning the webs such that their respective outer surfaces are in a facing relationship;

bonding the webs together at a plurality of locations in the longitudinal direction to define a plurality of crotch seams, creating an inside-out composite pant web;

repositioning the webs such that the inner surfaces are in a facing relationship, creating an outside-out composite pant web having a plurality of inward fin crotch seams spaced apart in the longitudinal direction;

bonding the webs together at a plurality of locations in the longitudinal direction to define a plurality or web side seams, each web side seam positioned longitudinal between a pair of crotch seams; and cutting the outside-out composite pant web into a plurality of disposable pants, each pant having a waist opening, two leg openings, two pant side seams, and an inward fin crotch seam.

14. The method of claim 13 wherein each web has a transverse width, and the first and second webs are unequal in width.

15. The method at claim 14 wherein the first end second webs are positioned such that their respective web waist edges coincide.

16. The method of claim 13 wherein bonding the webs together to define a plurality of web side seams comprises bonding two web side seams longitudinally between each pair of crotch seams, the first web remaining substantially unbonded to the second web in an area longitudinally between the two web side seams, and wherein the outside-out composite pant web is cut into a plurality of disposable pants along a cut line in the unbonded area.

17. The method of claim 13 wherein the crotch seam is an inset crotch seam, and the method further comprises removing sections of the first and second webs between each inset crotch seam and the web leg edges.

18. The method of claim 13 wherein comprising cutting at least one slit in each crotch seam.

19. The method of claim 18 wherein each slit passes completely through each of the first and second webs.

20. The method of claim 13 wherein comprising cutting at least one notch in each crotch seam.

21. A disposable pant having a waist opening, two leg openings and two side regions, the pant comprising:

front and back panels;

two side seams joining the front and back panels;

an inward fin crotch seam joining the front and back panels;

wherein the inward crotch seam includes at least one slit.

22. The disposable pant at claim 21 wherein the inward crotch seam includes at least five slits.

23. A disposable pant having a waist opening, two leg openings and two side regions, the pant comprising:

front end back panels;

two side seams joining the front and back panels;

an inward fin crotch seam joining the front and back panels;

wherein the inward crotch seam includes at least one notch.

24. A disposable pant having a waist opening, two leg openings and two side regions, the pant comprising:

front and back panels;

two side seams joining the front and back panels;

an inward fin crotch seam joining the front and back panels;

wherein the crotch seam follows a path that begins at one leg opening, extends toward the waist opening, and terminates at the other leg opening.

25. The disposable pant of claim 24 wherein the path is arcuate.

26. The disposable pant of claim 24 comprising an absorbent.

27. A disposable pant having a waist opening, two leg openings and two side regions, the pant comprising:

front and back panels;

two side seams joining the front and back panels;

an inward fin crotch seam joining the front and back panels; and an absorbent, wherein the absorbent comprises a front absorbent piece attached to the front panel and a back absorbent piece attached to the back panel, wherein the front and back absorbent pieces are not attached to each other.

28. The disposable pant of claim 27 wherein the front and back absorbent places contact each other near the inward fin crotch seam.

29. The disposable pant of claim 27 wherein the front end back absorbent pieces are contained within the respective front and back panels.

30. The disposable pant of claim 27 wherein the inward fin crotch seam has a height, and at least one of the front and back absorbent pieces has a thickness at an end that is closest to the inward fin crotch seam that is greater than the inward fin crotch seam height.

31. The disposable pant of claim 26 wherein the front and back panels each comprise an absorbent panel sandwiched between an outer cover and a liner.

* * * * *